(12) United States Patent
Waechter-Stehle et al.

(10) Patent No.: US 11,540,718 B2
(45) Date of Patent: Jan. 3, 2023

(54) IMAGING VIEW STEERING USING MODEL-BASED SEGMENTATION

(71) Applicant: KONINKLIJKE PHILIPS N.V., Eindhoven (NL)

(72) Inventors: Irina Waechter-Stehle, Hamburg (DE); Sabine Mollus, Aachen (DE); Christian Buerger, Hamburg (DE); Emil George Radulescu, Ossining, NY (US); Sheng-Wen Huang, Ossining, NY (US); Juergen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1766 days.

(21) Appl. No.: 15/103,053

(22) PCT Filed: Dec. 5, 2014

(86) PCT No.: PCT/IB2014/066618
§ 371 (c)(1),
(2) Date: Jun. 9, 2016

(87) PCT Pub. No.: WO2015/087218
PCT Pub. Date: Jun. 18, 2015

(65) Prior Publication Data
US 2018/0132724 A1 May 17, 2018

Related U.S. Application Data

(60) Provisional application No. 61/913,477, filed on Dec. 9, 2013.

(51) Int. Cl.
| | |
|---|---|
| A61B 5/00 | (2006.01) |
| A61B 8/00 | (2006.01) |
| A61B 8/08 | (2006.01) |
| G06T 7/73 | (2017.01) |
| A61B 34/30 | (2016.01) |
| A61B 8/06 | (2006.01) |

(52) U.S. Cl.
CPC .......... *A61B 5/0044* (2013.01); *A61B 8/0883* (2013.01); *A61B 8/429* (2013.01);
(Continued)

(58) Field of Classification Search
None
See application file for complete search history.

(56) References Cited

U.S. PATENT DOCUMENTS

| | | |
|---|---|---|
| 6,425,865 B1 | 7/2002 | Salcudean et al. |
| 2003/0167005 A1 | 9/2003 | Sakuma et al. |
| | (Continued) | |

FOREIGN PATENT DOCUMENTS

| | | |
|---|---|---|
| JP | 5344968 A | 12/1993 |
| JP | H05344968 A | 12/1993 |
| | (Continued) | |

OTHER PUBLICATIONS

Ecabert, et al., "Automatic Model-Based Segmentation of the Heart in CT Images", IEEE, vol. 27(9), pp. 1189-1201, 2008 (abstract).

*Primary Examiner* — Amelie R Davis
*Assistant Examiner* — Marjan Saboktakin

(57) ABSTRACT

An imaging steering apparatus includes sensors and an imaging processor configured for: acquiring, via multiple ones of the sensors and from a current position (322), and current orientation (324), an image of an object of interest; based on a model, segmenting the acquired image; and determining, based on a result of the segmenting, a target position (318), and target orientation (320), with the target position and/or target orientation differing correspondingly from the current position and/or current orientation. An electronic steering parameter effective toward improving the current field of view may be computed, and a user may be provided instructional feedback (144) in navigating an imaging probe toward the improving. A robot can be configured (Continued)

for, automatically and without need for user intervention, imparting force (142) to the probe to move it responsive to the determination.

19 Claims, 8 Drawing Sheets

(52) U.S. Cl.
CPC .......... *A61B 8/4218* (2013.01); *A61B 8/4245* (2013.01); *A61B 8/461* (2013.01); *A61B 8/5215* (2013.01); *A61B 34/30* (2016.02); *G06T 7/73* (2017.01); *A61B 8/065* (2013.01); *A61B 8/4427* (2013.01); *A61B 8/4488* (2013.01); *A61B 8/483* (2013.01); *A61B 8/5207* (2013.01); *A61B 8/5223* (2013.01); *A61B 8/54* (2013.01); *A61B 2576/023* (2013.01); *G06T 2207/10132* (2013.01); *G06T 2207/30048* (2013.01)

(56) References Cited

U.S. PATENT DOCUMENTS

| | | | |
|---|---|---|---|
| 2004/0019270 | A1 | 1/2004 | Takeuchi |
| 2008/0021317 | A1 | 1/2008 | Sumanaweera |
| 2008/0181479 | A1 | 7/2008 | Yang et al. |
| 2011/0079083 | A1* | 4/2011 | Yoo ..................... G01S 7/52073 73/632 |
| 2011/0087091 | A1* | 4/2011 | Olson ....................... A61B 8/08 600/437 |
| 2011/0246129 | A1 | 10/2011 | Ishikawa |
| 2012/0035481 | A1 | 2/2012 | Barbagli et al. |
| 2012/0071757 | A1 | 3/2012 | Salcudean et al. |
| 2012/0101388 | A1* | 4/2012 | Tripathi ............... A61B 8/4254 600/459 |
| 2015/0011886 | A1 | 1/2015 | Radulescu |
| 2016/0174934 | A1* | 6/2016 | Cong .................. A61B 8/4254 600/459 |

FOREIGN PATENT DOCUMENTS

| | | |
|---|---|---|
| JP | 2002253548 A | 9/2002 |
| JP | 2003135459 A | 5/2003 |
| JP | 2004016268 A | 1/2004 |
| JP | 2007312980 A | 12/2007 |
| JP | 2009056125 A | 3/2009 |
| JP | 2009082240 A | 4/2009 |
| JP | 2013135869 A | 7/2013 |
| WO | 2006114735 A1 | 11/2006 |
| WO | 2014097090 A1 | 6/2014 |

\* cited by examiner $$b(r,\theta) \equiv \frac{C[b_1(r,\theta), b_2(r,\theta)]}{\sqrt{C[b_1(r,\theta), b_1(r,\theta)]}\sqrt{C[b_2(r,\theta), b_2(r,\theta)]}},$$

where $$C[b_k(r,\theta), b_l(r,\theta)] \equiv \int_{-\infty}^{\infty}\int_{-\infty}^{\infty} w(r',\theta') b_k(r+r', \theta+\theta') b_l(r+r', \theta+\theta') dr' d\theta',$$

and where $$b_k(r,\theta) = \sum_{j \in c_k} s_j(r,\theta)$$

IMAGING VIEW STEERING USING MODEL-BASED SEGMENTATION

This application is the U.S. National Phase application under 35 U.S.C. § 371 of International Application No. PCT/IB2014/066618, filed on Dec. 5, 2014, which claims the benefit of U.S. Provisional Application Ser. No. 61/913,477, filed Dec. 9, 2013. These applications are hereby incorporated by reference herein.

FIELD OF THE INVENTION

The present invention relates to the steering of imaging and, more particularly, to using model-based segmentation in the steering.

BACKGROUND OF THE INVENTION

Heart failure is a major disease with five million patients in the United States alone and tens of millions worldwide. The individuals at risk of heart failure are estimated at 60 million in the United States only; one million are hospitalized, the rest being in the care of heart failure clinics. Basic information about the heart is needed in the heart failure clinics or general practitioners' offices for patient management. This information includes images as well as quantification data, such as ejection fraction, computed from the image once the image is acquired. Ultrasound is a reliable and cost-effective imaging modality for soft tissue such as the heart.

Acquisition of an ultrasound image requires a skilled sonographer. One parameter the sonographer, or other clinician trained in sonography, optimizes is the field of view. The apical four chamber view is a standard one for routine cardiac checkups. The clinician places the head of the ultrasound probe, or "transducer probe", on the patient. An effective site on the patient's skin for placement of the probe for various views is part of the clinician's training, and the site can vary from patient to patient. For the apical four chamber view the probe is placed over the apex of the heart. The probe also needs to be manually tilted, typically in different directions until the organ is captured for imaging. This is all done interactively, with the clinician viewing the image, which is usually a sonogram, on-screen. Interpreting a sonogram is a skill that must be developed, e.g., through training and practice. The clinician's experience tells him or her, in an ongoing iterative process, how to shift and tilt the probe to achieve an effective acoustic window.

SUMMARY OF THE INVENTION

What is proposed herein below is directed to addressing one or more of the above concerns.

Access to a full ultrasound scan in heart failure clinics and general practitioner's offices is not easy. Making the ultrasound system portable would help. However, although most cardiologists would be able to use a conventional portable ultrasound system, they are generally too busy to carry out this procedure themselves.

Yet, serial imaging, in which images of the heart are taken periodically for example, would improve patient treatment.

What is needed is a point-of-care solution that enables automatic ultrasound-based volumetric measurement of the heart during the patient's regular visit, which would be especially useful in heart failure clinics. A nurse trained in placing ECG leads, but with no training in echocardiography, would operate the portable system and the cardiologist would be provided with the diagnostic images together with automatic measurements such as ventricle size and ejection fraction.

As an alternative, a system fully automated to, itself, maneuver the ultrasound imaging probe would be of value.

Such technologies would lower the barrier to use of ultrasound data for cardiac diagnostic and follow-up examinations.

In accordance with an aspect of the present invention, an imaging steering apparatus is designed for: acquiring, via multiple sensors, and from a current position, and current orientation, an image of an object of interest; based on a model, segmenting the acquired image; and determining, based on a result of the segmenting, a target position, and target orientation, with the target position and/or orientation differing correspondingly from the current position and/or orientation.

For such a apparatus, a computer readable medium or alternatively a transitory, propagating signal is part of what is proposed herein. A computer program embodied within a computer readable medium as described below, or, alternatively, embodied within a transitory, propagating signal, has instructions executable by a processor for performing the acts of: acquiring, via multiple sensors, and from a current position, and current orientation, an image of an object of interest; based on a model, segmenting the acquired image; and determining, based on a result of the segmenting, a target position, and target orientation, with the target position and/or orientation differing correspondingly from the current position and/or orientation.

Details of the novel, real-time, user-pause-driven/robotic, acoustic-window identification guidance technology are set forth further below, with the aid of the following drawings, which are not drawn to scale.

DETAILED DESCRIPTION OF EMBODIMENTS

Figure 1:
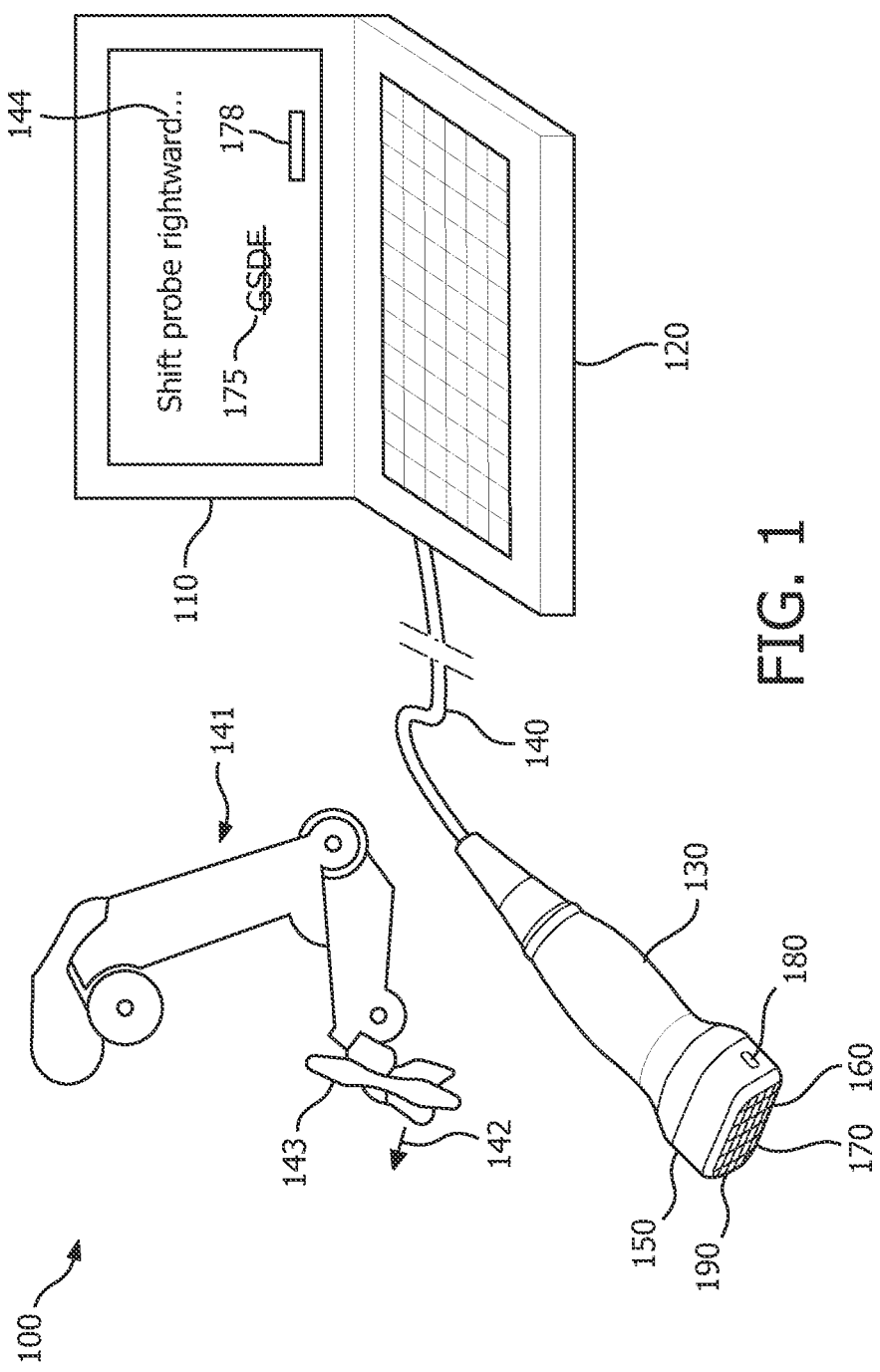
FIG. 1 is a perspective view of one form of an apparatus in accordance with the present invention.

FIG. 1 depicts a portable apparatus 100 as one example of an implementation of the novel, real-time, user-pause-driven, acoustic-window identification guidance technology proposed herein. Although shown here in a form factor easily transportable from room to room in a clinical environment, the apparatus 100 may instead be implemented as a stationary device. The apparatus 100 includes, in addition to an imaging processor (not shown), a display 110, a user console 120, a transthoracic echocardiography (TTE) probe 130, and a probe cable 140 of extended length as represented by the broken lines in FIG. 1. The display 110 and user console may be similar to those used in a laptop computer. At a total weight of about 10 pounds, the unit 100 can be carried by hand. The cable 140 may be omitted in a wireless implementation. The description below will assume an ultrasound system, although any kind of imaging system is within the intended scope of the invention. Also, although volumetric quantification and live three-dimensional imaging are features of the embodiment below, what is proposed herein applies also to two-dimensional imaging.

In a robotic, stationary version of the apparatus 100, a robotic arm 141 is controlled to impart force 142 to a probe 143 to move it from a current position and orientation to a target position and orientation. The probe 143 the robot maneuvers is the same as the handheld probe 130, although it can be adapted for robotics, e.g., by omitting user feedback features discussed below. The movement is caused responsive to the determination of the target parameters. The robot operates automatically and without the need for user intervention. There is, nevertheless, an optional user control or override.

The description below addresses the manual probe manipulation version, or "manual version", except where otherwise indicated, i.e., that the robotic version is being discussed.

The apparatus 100 is configured for using ultrasound to perform volumetric imaging, such as computing the size of the left ventricle of the heart or computing ejection fraction. The computation results are stored in a memory (not shown). Live imaging acquired via the probe 130, and upon which the computations are based, is also stored in memory. Circuitry (not shown) for standard functions such as dynamic beamforming, scan conversion and image rendering is also included within the apparatus 100. Two or more beamformers can be included for automatic image blockage detection, which is discussed further below.

Additional circuitry (not shown) may include a user-guidance processor configured for dynamically presenting visual feedback, i.e., user instructions. They are of a kind specifically for guiding manual adjustment, via the probe 130, of a position and orientation associated with the probe, and accordingly an acoustic window. It is computed how a three-dimensional field of view from a current position and current orientation of the probe 130, i.e., the current field of view, can be updated and thereby improved toward achieving a target position and target orientation. The update is based on one or more segments created by segmenting an image in the current field of view. The model upon which the segmentation is based can provide the updated, or "new", field of view, based on an optimum viewing directionality and a location of the segment(s); or, if moving the probe 130 to attain the directionality is, due to rib blockage, not feasible, the new field of view is based in part on the location of the segment(s).

The computation derives information which, in a manual embodiment, is presentable to a user to propose user action toward the improving of the field of view. The processor dynamically arranges the presentation, and selectively arranges it for guiding the user and in conformity with the field of view updates. The updated field of view, when compared to the current field of view, serves as the guidepost in notifying the clinician, untrained in sonography, on how to next manipulate the probe 130. The processor issues all instructions to the user on how to manually maneuver the probe 130 to iteratively achieve the optimal acoustic window. Application of what is proposed herein is not confined to cardiac or medical examination; instead, any object subject to image segmentation to determine the orientation of the object is usable for view navigation. Thus, any object of interest, other than merely a sphere, is potentially usable in this manner.

The robotic version includes, in addition to the robotic arm 141 described herein above, the control system 4, and optionally the user control 3, described in commonly-assigned U.S. Patent Publication No. 2010/0262008 to Roundhill, the entire disclosure of which is incorporated herein by reference. The robotic arm 141 is implementable as the robotic armature in Roundhill. The Roundhill user control 3 can be made operable from the user console 120.

Segmentation need not be as detailed for the above-described "steering" of the field of view as it is for quantification once the target acoustic window is achieved. An example of model-based segmentation that uses coarse and fine meshes is found in commonly-assigned U.S. Patent Publication Number 2009/0202150 to Fradkin et al. ("Fradkin"). The adaptation termination criterion in Fradkin can be set to keep segmentation coarse for field-of-view steering in the present embodiment of apparatus 100, or set to proceed to fine segmentation for volumetric-data-based quantification in the present embodiment. Steering and quantification are discussed further below.

In order to locate an image for segmentation, the apparatus 100 is further configured for performing a generalized Hough transform (GHT). A method for performing a GHT is discussed in commonly-assigned U.S. Patent Publication No. 2008/0260254 to Schramm et al.

The entire disclosure of both publications is incorporated herein by reference.

The apparatus 100 further has, at least in the manual version, the capability of detecting motion of the probe 130. The user will often pause movement of the probe so that image segmentation can occur. Also, the apparatus 100 will check on whether an instruction to pause, e.g., because the probe 130 is close to attaining a target acoustic window, has yet been followed. In one embodiment, the apparatus 100 includes the increment calculator 80 disclosed in commonly-assigned U.S. Pat. No. 5,529,070 to Augustine et al. ("Augustine"). The increment calculator 80 is supplied values by means of the probe cable 140 that originate from accelerometers (not shown) residing in the probe 130. Unlike in Augustine, the positional readings need not be matched with image acquisition. So, the increment calculator can be simplified to merely detect movement in location and/or orientation of the probe 130. The accelerometers can be apportioned between the distal and proximal parts of the probe 130, as seen from FIGS. 4, 5 and 5a of Augustine. The entire disclosure in Augustine relating to the accelerometer embodiment is incorporated herein by reference. Alternatively, an example of using electromagnetic (EM) sensors in tracking a medical tool is provided in commonly-owned U.S. Pat. No. 7,933,007 to Stanton et al. A similar system which also attaches to the tool an optical sensor is disclosed in commonly-owned U.S. Patent Publication No. 2010/0168556 to Shen et al. Motion may also be sensed by comparing successive real time images as described in commonly-owned U.S. Pat. No. 6,299,579 to Peterson et al. All three documents are incorporated herein by reference in their entirety.

The above functions for which the apparatus 100 is configured may be implemented with any suitable and known combination of software, firmware and hardware. For example, the user-guidance processor and the control system may be realized on a device having one or more integrated circuits, or as a suitably programmed computer readable medium.

The probe 130 has a head 150 containing a matrix array 160 that includes transducer elements 170. Each element 170 functions, on receive, as a sensor. Although, for simplicity, a relatively small number of elements 170 are shown in FIG. 1, the number might typically be in the thousands. Also, although the array 160 is shown as generally rectangular, it might be square, circular, oval or in another shape. It also might be flat, as in a linear array, or curved, as in a curvilinear array.

Shown for purposes of illustration, on the display 110, is visual feedback 144 of kind specifically for guiding manual adjustment, via the probe 130, of the array's position and orientation. Advantageously, a user untrained in sonography need not rely on grayscale images, such as sonograms, for guidance. So, there is no reliance on a grayscale display function (GSDF), as represented by the on-screen annotation 175 that is struck out and depicted in FIG. 1. In particular, the visual feedback 144 of the embodiment shown in FIG. 1 does not include a grayscale depiction of image data acquired via the probe 130. Another example of visual feedback 144 is the on-screen overall progress bar 178. It can be annotated with a percentage such as "82%" or it can be progressively filled in and bordered by a frame that represents 100%, i.e., completion.

The probe 130 also has a pair of pause/go indicator lights 180 (one of which is visible in FIG. 1, with the other on the opposite side of the probe) realizable as a red/green light-emitting diodes (LEDs). When green, the light 180 indicates that the user should look to the display 110 for directions and then proceed by moving the probe 130 as instructed. When red, the light 180 indicates that the user should pause movement of the probe 130. Both lights are concurrently the same color.

As an alternative for the lights 180, or as an implementation of additional lights, directional indicator lights can be provided. In this alternative embodiment, when one light is green, the other is red. When green, the light indicates that the user should shift in the direction of the green light beam. The apparatus 100 will already have determined that the probe 130 is validly positioned along the intercostal space between the two ribs currently surrounding the matrix array 160, as discussed further below. Conversely, when red, the light indicates that the user should shift in the opposite direction. Since in this embodiment, there is no red light to indicate "pause", this function can be provided by an auditory signal, such as a beep, or an audible instruction, and can be accompanied by a visual indication on the display 110. Also, although here directional indicator lights are provided, the instruction to shift, and the directionality, may additionally appear on the display 110 and/or be communicated by artificial speech.

The probe may also incorporate an acoustic coupling quality sensor (not shown). Distributed sparsely among the transducer elements 170, i.e., in replacement of individual elements, are pressure sensors 190 devoted to detecting pressure. Detection may be interleaved with image acquisition. When transducer elements 170 in proximity of a pressure sensor 190 are active, and the pressure sensor reading implies lack of pressure, this indicates weak acoustic coupling. More generally, if and when the apparatus 100 decides, based on output of the acoustic coupling quality sensor, that acoustic coupling quality is insufficient, a user alert is issued upon that decision. Visual or auditory user alerts can be provided, via the probe 130 or other parts of the apparatus 100. As an example, the acoustic coupling quality sensor can comprise merely 8 pressure sensors 190 that are disposed among 10,000 transducer elements 170. In the robotic version, the acoustic coupling quality sensor is part of the Roundhill control system 4, i.e., the control feedback mechanism that includes applied force sensing. For the force sensing, strain gauges may be provided longitudinally in an axial direction of the probe 143, within the housing shallow beneath the surface, arranged spaced apart circumferentially around the probe, and disposed near the distal tip of the probe. An example of a similar strain gauge configuration is provided in FIGS. 2 through 7 of United States Patent Publication No. 2007/0151390 to Blumenkranz et al., the entire disclosure of which is incorporated herein by reference. Similar configurations of the gauges can be incorporated also or instead into the robotic arm 141. The axial strain readings of the gauges are usable in making, responsive to the readings, automatic small comfort adjustments during the examination procedure without losing acoustic coupling to the patient.

Figure 2A:
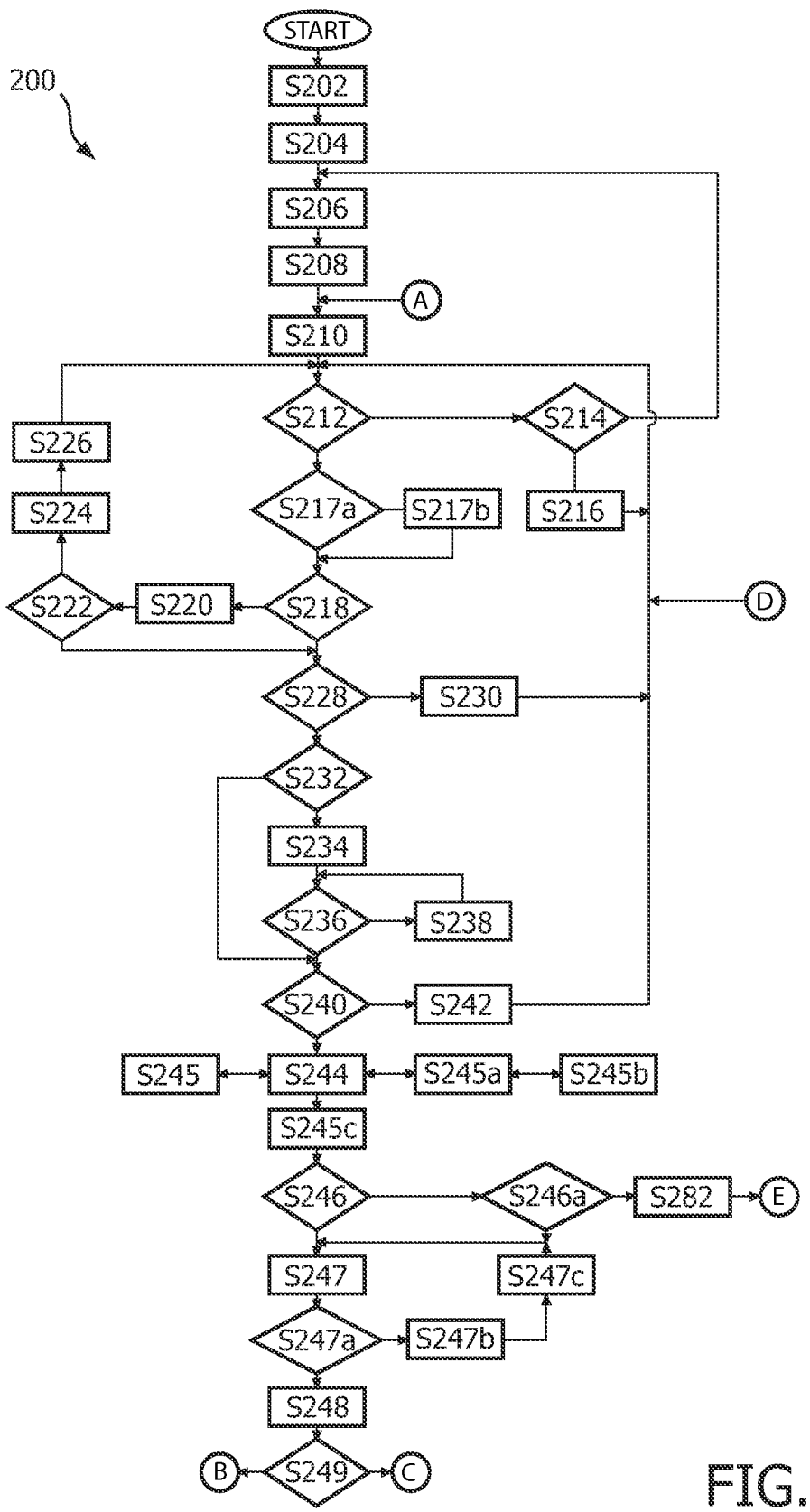
FIGS. 2A and 2B are flow charts of an exemplary ultrasound clinical procedure in accordance with the present invention.
Figure 2B:
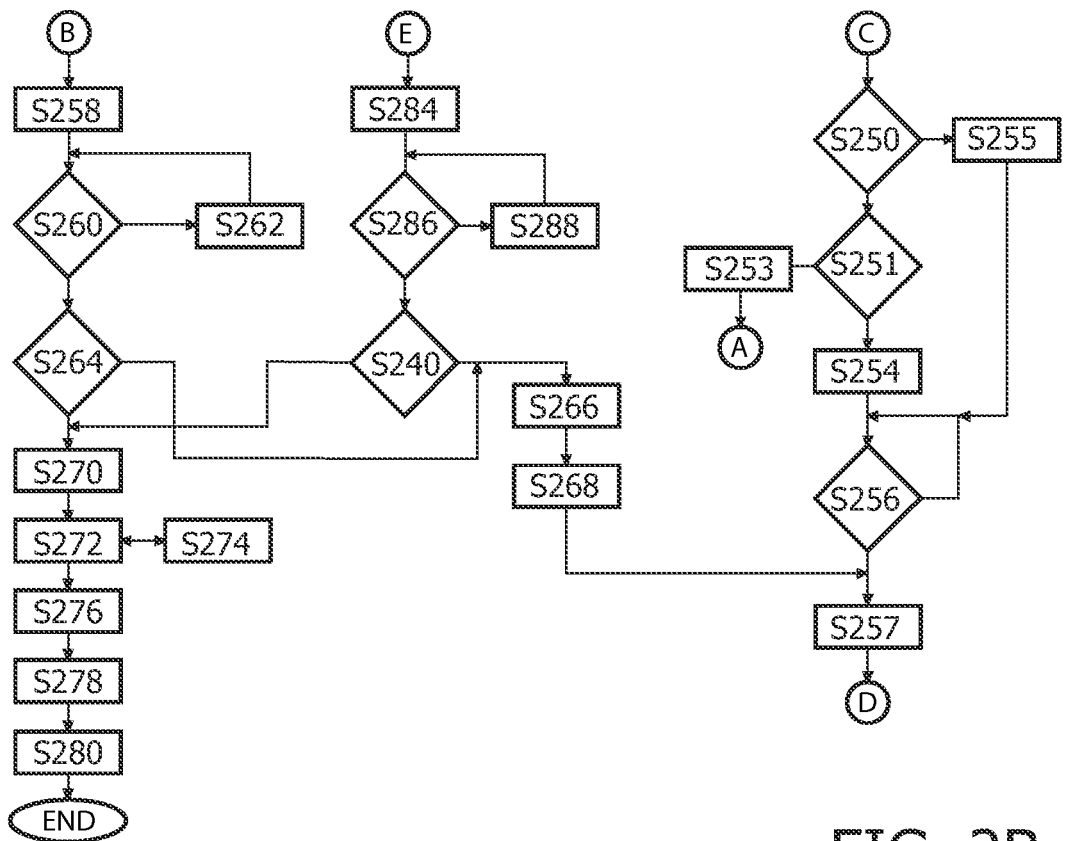

FIGS. 2A and 2B depict, by way of illustrative and non-limitative example, a clinical ultrasound procedure 200 demonstrating how the apparatus 100 visually guides a nurse, or other user, unskilled in sonography. In this embodiment, a four-chamber apical view of the heart for imaging is to be recorded and volumetric cardiac measurements are to be taken and stored. The process is in two stages. In the first stage, the user moves the probe 130 until the imaging detects at least part of the heart, or other organ of interest. In the second stage, the user moves the probe 130, pausing frequently and receiving further instructions shortly after each pause. Sometimes, the apparatus 100 determines that a transition is to be made, from the second stage, back to the first stage. Successful completion of the ultrasound procedure 200 occurs during, i.e., at the end of, the second stage. It is assumed for the procedure 200 that, except where otherwise indicated, the probe 130 maintains a geometrically-fixed field of view, and that electronic steering is not implemented or is not used to achieve a better view. Thus, navigation of the probe 130 relies on hand movement by the user. Electronic steering to improve the view, and a robotic version of the procedure, will be discussed further below.

Operationally, first, the nurse places the electrocardiogram (ECG) leads on the patient or ultrasound subject, human or animal (step S202). The ECG will serve as part of the cardiac checkup. It also facilitates analysis of the live cardiac imaging that will be recorded. At the outset, the user is instructed generally about the imaging that is to be done; that instructions will be visible on the display 110 and via the lights 180; to stop movement of the probe 130 promptly when instructed; and, when instructed to move the probe, to pause frequently so that the system can take readings (step S204). Also, a stage two flag is cleared as part of the initialization, since the user is initially in stage one of the procedure 200. The user is then instructed to have the patient lie on his or her left side, so that the heart will fall forward in the patient's chest for easier imaging (step S206). The user is instructed to start from the bottom of the rib cage at a point below the left nipple, and to count up to between the fourth and fifth ribs from the bottom of the rib cage (step S208) for a point at which to place the head 150 of the probe 130 for an initial acoustic window. Image acquisition by the probe is live and continuous. The instructions also mention that the probe should be tilted upward to point toward the base of the patient's neck as a first estimate. The instruction now is to: remembering the placement, lift away the probe 130; apply coupling gel around the probe face covering the matrix array 160; and reassume the probe placement as to location, and as to orientation (step S210). If, by a blockage-identification algorithm discussed further below, no ribs are detected (steps S212, S214), a branch back is taken to step S206. Otherwise, if only one rib is detected (step S214), the user is instructed to shift up or down slightly to get between the two ribs (step S216). On-screen, a graphic depiction can be displayed of a probe aimed at one rib being shifted up/down to placement between two ribs. Processing returns to step S212. In this processing loop, and all processing loops that involve issuing a user instruction, the instruction is not listed again if already shown on-screen. If, on the other hand, both ribs are detected (step S212), then this aspect of correct probe placement is validated. If a rib measurement flag is set (step S217a), processing skips to step S218. Otherwise, if the rib measurement flag is not yet set (step S217a), rib measurement is taken (step S217b). In particular, based on a distance between the two ribs, i.e., intercostal rib-to-rib spacing, gleaned automatically from the imaging, a rib width is estimated. The estimation may be done with reference to a statistical atlas or otherwise via analysis or table lookup. The estimate may be utilized to alter the target viewpoint of the apical view in the event the ideal viewpoint, i.e., aligned with the optimum viewing directionality, computed from the anatomical model at a later stage in the procedure 200, is blocked by a rib. Optionally, a blockage identification algorithm can be applied, by electronic steering if available, multiple times for a corresponding multiple consecutive number of ultrasound sector scans over an angular range, relative to the current position of the probe 130, that sweeps longitudinally across the current intercostal space. For each scan, a rib-to-rib distance is measured. Query is then made as to whether a lung is blocking the current field of view of the probe 130 (step S218). This determination is made by a blockage-identification algorithm discussed further below. If lung tissue is in the field of view (step S218), the user is instructed to have the patient exhale and hold his or her breath (step S220). This might take the lung out of the field of view, since the lung may venture in and out of the field of view with each breath and expiration by the patient. If the lung is detected again and therefore is still blocking the field of view (step S222), the user is instructed to have the patient resume normal breathing (step S224). Since the lung blocking the heart would be the left lung and since the lung is less central on the chest than is the heart, the user is instructed to shift the probe 130 upward, i.e., toward the breastbone (step S226). The pause/go indicator lights 180 on the probe 130 will be green. The user may also be told to tilt the probe 130 slightly to aim more to the left side of the patient, as the probe is shifted up. Return is made to step S212. Alternatively or in addition, the user may be shown an on-screen inverted "V" display by which the user can interactively shift and tilt the probe 130 to avoid the lung. The same "V" display could be used to guide the user to tilt and translate the probe 130 to avoid the ribs. If, on the other hand, after having the patient hold his or her breath (step S220), the lungs are no longer blocking the field of view (step S222), or if the lungs were not initially blocking (step S218), query is made as to whether at least part of the heart is detected in the live imaging by the probe 130 (S228). The Schramm GHT, mentioned above, is utilized for this detecting. The GHT is used to localize the object of interest, or anatomy of interest. Although the left ventricle (LV) may be the part of the heart for which quantification is desired, detecting part of the heart can even involve detecting merely the left atrium, or the mitral valve, for example. A predetermined confidence level must be met in deciding whether the detection has occurred. For example, in the Schramm reference the measure of optimality in determining the set of transformation parameters can be required to meet a predetermined threshold.

If the heart is not detected (S228), the user is instructed to "Shift slowly down away from the breastbone, shift slowly up toward the breastbone, each time to a greater extent." A graphic moving depiction of the pattern may be displayed on the display 110 (step S230). The instructions can alternatively be more detailed, such as "Alternate by shifting the probe 130 slowly down away from the breastbone while staying in the intercostal space and shifting slowly back up toward the breastbone, each time to a greater extent." The user might, instead of strictly translating the probe 130, translate it while slowly changing its orientation. This will be alright, because the live imaging is dynamically monitored to deliver real-time feedback based on the current location and pose of the probe 130. The procedure 200 branches back to step S212.

If, on the other hand, part of the heart is detected (step S228), query is made as to whether the stage two flag, which was cleared during initialization in step S204, is set (step S232). If it is not set (step S232), the user is instructed to pause and wait for instructions (step S234). The pause is needed, because segmentation, even coarse segmentation, requires a short time period, e.g., two seconds. Specifically, the pause/go indicator lights 180 on the probe 130 will turn red and/or the display 110 will show, in red, an instruction to pause. A short audio beep may also issue. The apparatus 100 detects, via the accelerometers in the probe 130, whether motion of the probe has paused (step S236). Until the movement pauses (step S236), the visual and audio feedback to pause is maintained (step S238). When a pause is detected (step S236), a check is again made as to whether part of the heart is detected (step S240). This precaution is taken to determine whether the user has paused quickly enough to still be imaging part of the heart.

If there no longer exists detection of part of the heart (step S240), the instruction (step S242) is "Slowly backtrack your most recent movement and pause when instructed to regain (partial) view of the heart . . . otherwise shift as instructed." Return is then made to step S212.

On the other hand, if at least part of the heart is still detected (step S240), a coarse image-segmentation of the bodily organ, here the heart, is performed (step S244) using a model (step S245). In particular and by way of example, an attempt is made to segment the left ventricle endocardium (step S245a) and the myocardium surrounding the left ventricle (S245b). A confidence for the segmentation result may be assessed based, for example, on an error metric (step S245c).

Query is made as to whether the anatomy, judging from the segment(s), is entirely or mostly within the current field of view of the probe 130 (step S246). The judgement is refinable through the use of the blockage-identification algorithms, discussed further below, that define areas of blockage. In particular, the algorithms allow portions of the ultrasound sector scan to be marked as unreliable, i.e., areas of the image having artifacts due to blockage of the imaging by a lung or rib for example. The decision on whether the left ventricle endocardium and the surrounding myocardium are, for the most part, covered in the field of view can then be made relative to the reliable areas of the image.

If the segmentation result is that collectively this anatomy is not mostly within the current field of view (step S246) or there is a lack of confidence in the segmentation (step S246a), a coordinate system transformation is computed (step S247). In particular, the coarse segmenting has produced one or more segments of the heart having a location and optimum viewing directionality in the image space of the probe 130. The location and directionality are known from the model. Based on the location and directionality, it is determined what would be an optimal viewpoint and viewing orientation for a geometrically-fixed field of view of the probe 130 that covers the anatomy, e.g., the left ventricle, being investigated. For example, both the mitral valve and the apex of the heart can be identified by the segmentation, and an axis connecting them may be, or may be close to, an optimal viewing orientation for quantification and diagnostic cardiac images. This optimal viewing orientation is made the target orientation. In effect, the apparatus 100 creates, from the model, an axis. The determining of the target orientation is such as to align it with the axis. The target position is computed based on this orientation, taking into account longitudinal curvature of the ribs. The field of view is geometrically fixed, because it is assumed that the user is untrained in sonography and, for simplicity, is being guided merely to move the probe 130 according to visual instructions. The target position, or "viewpoint", and the target orientation will, in general, differ from the current position and current orientation. However, if, for example, the apex is underneath the focus, the current viewpoint may be the target viewpoint. The viewpoints and orientations are all in the image space of the probe 130. The apparatus 100 computes a coordinate system transformation that would bring the current viewpoint and orientation into coincidence with the target viewpoint and orientation. The transformation has a translational component and a rotational component. The rotational component corresponds to an angle between the current probe z-axis, i.e., the axial direction of the probe 130, and the above-mentioned model-based axis connecting the center of the heart apex and the mitral valve. More specifically, if the z-axis is translated laterally and/or elevationally, while maintaining the same direction, to intersect the model-based axis, the angle between the two axes represents the rotational component. The target viewpoint can be estimated as the intersection of the model-based axis with a plane along the face of the probe 103, optionally with a slight adjustment for longitudinal curvature of the ribs along the intercostal space. The translational component is the vector from the current viewpoint to the target viewpoint. Rib curvature may be empirically estimated. It diminishes as a factor as the optimal view is iteratively acquired, since the curvature operates over a smaller and smaller area as the optimal view is honed in on.

Due to anatomical differences among individuals, the apical view found by the model may have a target viewpoint that is, in actuality, blocked by a rib. Query is made as to whether, based on the intercostal rib-to-rib spacing measurement(s), the consequent estimate of rib width, the ribs visible in the current field of view, and the current viewpoint, the target viewpoint is blocked by a rib (step S247a). If the target viewpoint is blocked by a rib (step S247a), the model-based axis is revised (permanently for the present examination), by replacing it with a line from the center of the heart to the current position (step S247b) and making the current position the target position (step S247c). Return is made to the transformation step S247. The transformation step may then, in computing a target orientation arrive at an orientation that differs from the current orientation, since the current orientation may be off-center with respect to the heart. Thus, based on an assessment of rib blockage, the apparatus 100 decides whether to make the current position the target position in a repetition of the determining of a target orientation. Alternatively for step S247c, a model-based axis revision (likewise permanent for the current examination) can be made by rotation just past the blocking rib. This rotation is based on the above-noted measurement to see whether blocking by a rib exists, and the estimated rib width. Return is likewise made to the transformation step S247.

After the transformation, with correction if appropriate, is computed (step S247a), the on-screen overall progress bar 178 is updated (step S248).

The progress is based on the magnitude of the translation component of the transformation and, to a lesser degree or at a later stage, on the magnitude of the rotational component of the transformation.

The length of the progress bar 177 could therefore be, percentage-wise, 100 minus a weighted average of the two components that is non-negative and less than unity.

The same or a similar metric is used by the apparatus 100 to decide whether the current view is sufficiently on target, i.e., close to the optimal field of view, for commencing quantification and optionally live imaging acquisition for storage.

If it is determined that the current field of view of the probe 130 is not sufficiently close to the optimal field of view (step S249), a decision is made as to whether tilting or shifting predominates as the selection for the next user instruction (step S250). Generally, shifting will predominate if any remains; although, if the remainder is small enough, tilting may be sufficient. The parameters for making the decision can be empirically established. Thus, it is decided whether shifting or tilting will be of greater effect. Going forward from this point in the procedure 200, presentation to the user of the visual feedback 144 is dynamically arranged selectively based on a comparison between the current field of view of the probe 130 and the target position and target orientation from step S247. For example, it is based on the need for shifting and/or tilting, those needs being assessed based in the comparison. The selecting inherently occurs according to which of the user instructions mentioned below issues in the procedure 200. It is noted here that the arranging of the presentation of visual feedback 144 earlier in the procedure 200, such as in the steps S212-S228, is done dynamically and selectively and is based on image content acquired but not on the above-mentioned comparison. Therefore, some but not all of the dynamic, selective arranging of visual feedback 144 within the procedure 200 is based on the comparison.

If shifting predominates (step S250), query is made as to whether the translation indicated would involve crossing a rib to enter an adjoining intercostal space, given the position of the ribs (step S251). The apparatus 100 has already determined this by virtue of the transformation computation (step S247) potentially supplemented by a corrective translation (step S247b, S247c). If a rib is to be skipped (step S251), the user is accordingly instructed to, after re-applying coupling gel to the probe 130, move up, or down, the ribcage (step S253). Since a rib has now been skipped, as a precaution processing goes back to stage one. The stage two flag is cleared, and processing returns to step S210. If, on the other hand and as is typically the case, the examination remains in the same intercostal space (step S251), the user is instructed to shift slowly in the direction determined by the apparatus 100, pausing frequently (step S254). Thus, this user instruction is among those dynamically and selectively arranged based on the above-mentioned comparison.

If, on the other hand, shifting does not predominate in step S250, the user is instructed to tilt the probe 130 slowly in the determined direction (step S255). The instruction may be "tilt slowly aiming inward toward the breastbone, stopping frequently" or "tilt slowly aiming downward toward the patient's feet, stopping frequently", some combination of these two instructions, etc. This instruction then is among those dynamically and selectively arranged based on the above-mentioned comparison.

Alternatively or in addition, the display 110 may show an interactive graphical depiction of the segmented organ, here segments defining a heart, as a segmented on-screen object with a superimposed, inverted "V" representing the field of view of the probe 130. A second, separate, concurrent depiction may be shown for a "V" in the orthogonal direction. This graphical depiction is discussed further below.

After the instruction for either step S254 or S255 issues, query is made as to whether movement since step S236 has occurred. This can be determined via the accelerometers in the probe 130. If such movement has occurred and if there is no movement now (step S256), the stage two flag is set (step S257), and processing returns to step S212.

If, on the other hand, it is determined in step S249 that the current field of view of the probe 130 is sufficiently close to the optimal field of view, the apparatus 100 issues an instruction to halt (step S258). Specifically, the pause/go indicator lights 180 on the probe 130 will turn red and/or the display 110 will show, in red, an instruction to halt. A short audio beep may also issue. The apparatus 100 detects, via the accelerometers in the probe 130, whether motion of the probe has halted, i.e., paused or terminated (step S260). Until the movement halts (step S260), the visual and audio feedback to halt is maintained (step S262). Once the movement halts (step S260), query is made, as in step S249, as to whether the current view is sufficiently on target for commencing quantification and optionally live imaging acquisition for storage (step S264). If the current view is not, i.e., is no longer, on target (step S264), the progress bar 178 is accordingly shortened to reflect the setback in progress toward completion of the procedure 200 (step S266). An instruction issues for the user to slowly backtrack the most recent probe movement, stopping frequently (step S268). Processing branches to step S257. If, on the other hand, the current view is sufficiently on target for commencing quantification and optionally live imaging acquisition for storage (step S264), the user is notified to hold the probe 130 still for completion of the procedure 200 (step S270). Fine segmentation is performed for quantification (step S272). The model is utilized for this purpose (step S274). The apparatus 100 starts recording live imaging of the heart or heart section (step S276). If the apparatus 100 includes an electronic steering capability, various views of the heart such as the standard views can be played back from the recording. The apparatus also makes volumetric measurements from the segmentation (step S278). For example, LV size is computed, over a heart cycle, by finding the average or maximum length and finding the average or maximum breadth, or directly using the coordinates of the points in the final mesh of the segmentation. Likewise, ejection fraction is computed by detecting, over a cardiac cycle, minimum and maximum LV volume, and subtracting a ratio of the two quantities from 1. The quantification data is stored in memory (step S280).

Referring again to step S246, if the segmentation result is that the heart is, in fact, entirely or mostly within the current field of view (step S246) and confidence exists in the segmentation (S246a), the progress bar 178 is made to reflect near completion (step S282). An instruction to halt is given in step S284. While movement of the probe 130 is detected (step S286), a user alert to halt is maintained (step S288). Once it is detected that the probe 130 is halted (step S286), query is again made as to whether the heart is entirely or mostly within the current field of view (step S290). If the heart is entirely or mostly within the current field of view (step S290), processing branches to step S270 to instruct the user to pause for completion of the procedure 200. Otherwise, if the heart is no longer entirely or mostly within the current field of view (step S290), processing branches to step S266 to try to recover the image of the heart.

Figure 3:
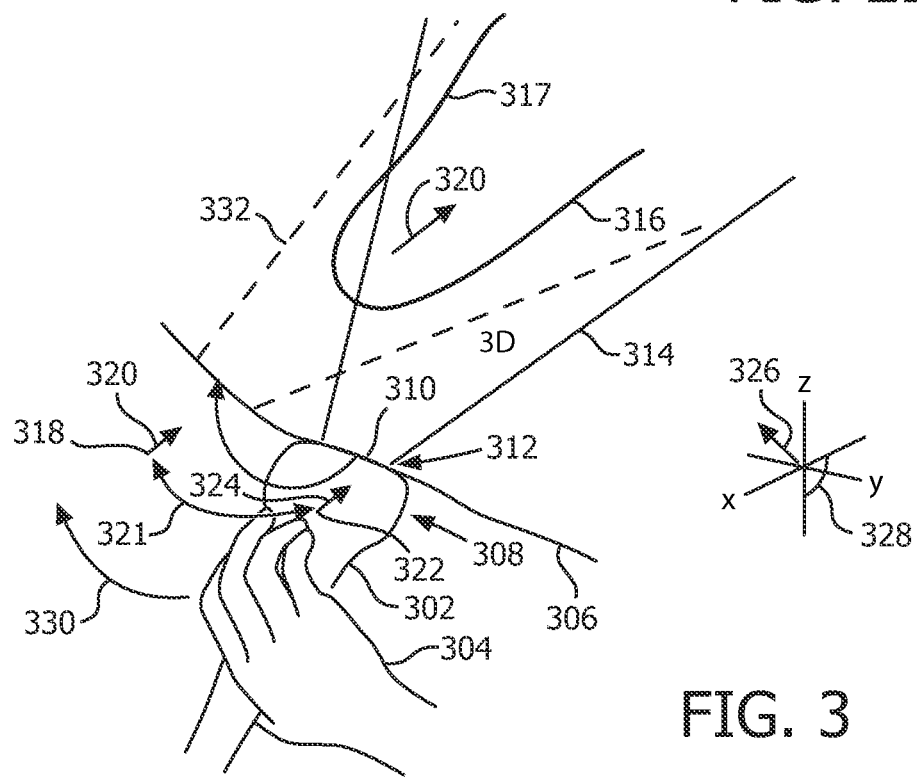
FIG. 3 is a conceptual diagram of how the apparatus is able to guide, in real time, the placement of the acoustic window.

FIG. 3 depicts, conceptually, how the apparatus 100 is able to guide, in real time, placement of the acoustic window. A probe 302 is held by the clinician's hand 304 against the skin 306 of a patient. More specifically, the probe 302 has a head 308 which has a face 310 for placement against the skin 306, separated from the skin only by the acoustic coupling medium such as a specialized gel. Within the head 308 and along the face 310 is a matrix array 312. Extending from the matrix array 312 is a field of view 314. In the present example, the field of view 314 is three-dimensional. This is noted in FIG. 3, by the symbol "3D", although the intended scope of the invention is not limited to three-dimensional imaging and can, for example, encompass two-dimensional imaging. The heart 316 of the patient is partially, here mostly, within the field of view 314, and is being imaged via the probe 302. Since part of the heart 316 is detected with a sufficient level of confidence, the clinician has been instructed to pause and has done so promptly. As a result of image segmentation into segments 317, the apparatus 100 determines, via the model, an orientation 320 that would provide an optimal, or targeted, view of the heart 316 if the probe 302, or some part of the probe such as the matrix array 312, were to assume that orientation from an appropriate location 318. The model also provides the location 318. For simplicity of explanation, a curved arrow 321 in FIG. 3 starts at a location 322 and orientation 324 of the probe 302. The arrow 321 ends at the model-provided location 318 and model-provided orientation 320 that are derived from the image segmentation. The curved arrow 321 represents comparison of the field of view 314 with the model-provided location and orientation 318, 320. The comparison involves a coordinate system transformation that would bring the model-provided position and orientation 318, 320 into coincidence with the current position 322 and current orientation 324 of the probe 302. The transformation has a translational component 326 and a rotational component 328. Visual feedback 144 in the procedure 200 is selected based on magnitudes of the components 326, 328, as for example in steps S248, S249 and S264 of FIGS. 2A and 2B. Another curved arrow 330 in FIG. 3 shows the clinician's hand 304 maneuvering the probe 302, based on the feedback 144, into an apical view 332.

In the depicted example, the heart 316 is partially outside the current field of view 314. It is possible to use, if implemented, electronic steering, to improve a view so as to, as some point relatively advanced in the procedure 200, achieve the target view without having to manual move the probe 302. In computing how a current field of view is improvable, electronic steering parameters, such as a receive-beamforming channel delay, are computed. In the present example shown in FIG. 3, however, electronic steering into a favorable field of view corresponding to the apical view 332 still fails to capture imaging content that was out of view prior to the electronic steering. Accordingly, relying on electronic steering in the depicted example to shorten the procedure 200 might compromise the result, depending upon the impact of not having that particular image content. In particular, if the unavailability of the content results in a view of less than most of the left ventricle endocardium and myocardium surrounding the left ventricle, then electronic steering would not be, in and of itself, sufficient to attain an apical view for ejection fraction computation.

If, however, FIG. 3 were to be redrawn with the heart 316 completely within the current field of view 314, electronic steering proceeds as described immediately herein above, provided that the apparatus 100 has an electronic steering capability. Thus, the apical view 332 is achieved without maneuvering the probe 302, that maneuvering being represented by the curved arrow 330. Instead, it is achieved by electronic steering. Although the manual maneuvering of the probe 302 may have been needed earlier in the procedure to achieve detection of part of the heart 316 (step S228), electronic steering can, once it is employed to bring the entire, or most of the, left ventricle endocardium and the surrounding myocardium into into view, alleviate the need for further manual maneuvering of the probe 302.

Advantageously, the user is guided throughout a procedure for achieving an apical view of the heart.

In the robotic version which is discussed briefly herein above, all of the above methodology for providing feedback to the user is unnecessary to the extent the robotic version operates automatically. Likewise, features such as the indicator lights 180 for providing user feedback can be omitted. Similarly too, the monitoring of user pausing and movement of the probe 143 is not needed. In addition, in the robotic version, there is no need to determine whether translation of the probe 143 or tilting would be of greater effect, since the robotic version can effectuate both components of the transformation simultaneously. Also, the steps in FIG. 2A up until and including step S210 are user steps that are retained even in the robotic version. They are accompanied by the initializing procedures for the robotics, such as the user placing the probe 143 into the grasp of the robotic arm 141.

As mentioned herein above, detecting that the ribs bordering the current intercostal space are within the field of view is part of the validation that the current acoustic window, placed in finding an optimal acoustic window, is valid. User instructions on how to maneuver the probe 302 around the lungs to view the heart are also mentioned herein above.

Echocardiography is challenging as the heart is surrounded by ribs and lung tissue. Ultrasound can hardly penetrate calcified ribs (typically encountered in the apical view) and lung tissue because of severe acoustic impedance mismatch between them and other soft tissues. In addition, ultrasound absorption in ribs is quite high compared to tissue. Conventionally, optimization of ultrasound image quality is done solely by the user based on real-time-displayed grayscale ultrasound images on the screen. Though experienced users are usually capable of recognizing image degradation and improving image quality accordingly by moving the probe 302 to a better position, less experienced users might acquire compromised images because of inferior hand-eye coordination and less awareness of artifacts. Successful ultrasound scanning strongly relies on training and experience of the user. To help inexperienced or less experienced users acquire meaningful information from the heart using echocardiography, an anatomically intelligent ultrasound system is desired.

Since ultrasound can hardly penetrate a calcified rib, deep echoes of an ultrasound beam hitting a calcified rib are very unlikely to be from tissues under the rib. Rather, they might be picked up by sidelobes. The visual artifact is recognizable by an experienced sonographer viewing the (grayscale) sonogram, but can easily be unrecognized by the inexperienced user.

Also, to get good image quality for an inexperienced user, an ultrasound system should be aware of the presence of lung tissue.

One blockage-identification algorithm described below is specialized for detecting lung tissue, and especially rib tissue, blocking the field of view. A second blockage-identification algorithm described below is tailored especially for detecting lung tissue blockage. They are discussed in view of the following drawings. More detailed discussions of these algorithms are found in commonly-owned patent applications entitled "Rib Blockage Delineation in Anatomically Intelligent Echocardiography" and "Lung Tissue Identification in Anatomically Intelligent Echocardiography."

Figure 4A:
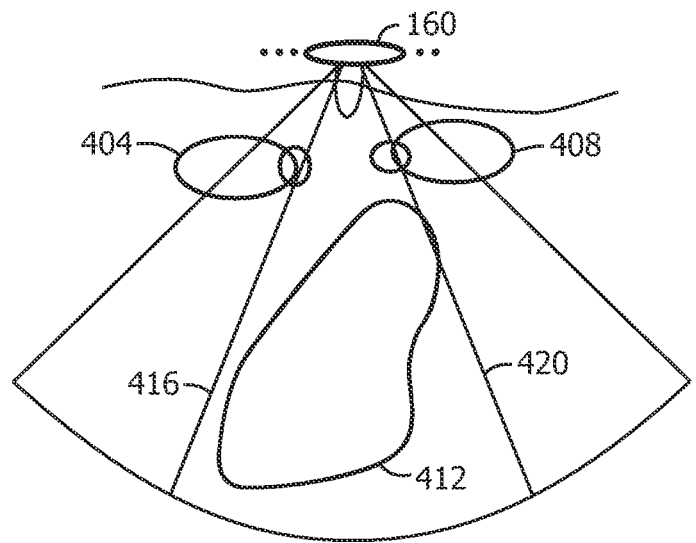
FIGS. 4A and 4B are diagrams showing examples of schemes for imaging-blockage avoidance that use on-screen guidance images of segments disposed with respect to a field of view of an ultrasonic probe, in accordance with the present invention.
Figure 4B:
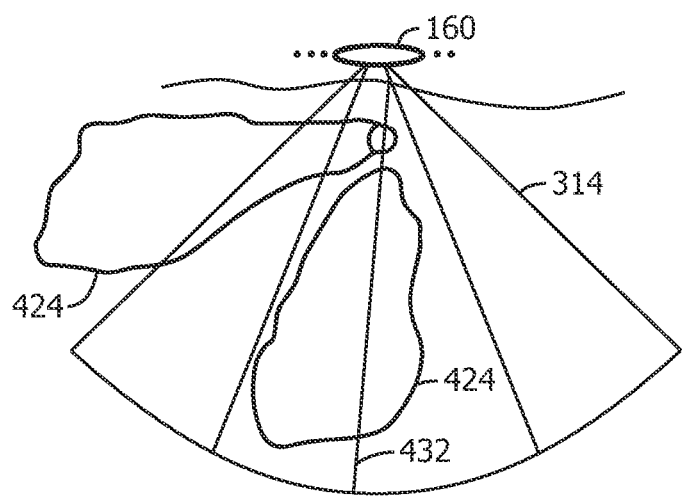

FIGS. 4A and 4B show examples of schemes for imaging-blockage avoidance that use on-screen guidance images of segments disposed with respect to a field of view of an ultrasonic probe 302.

Both figures feature a sonogram and in particular a sector scan. The FIG. 4A sonogram is an image slice that runs along the length of a patient; whereas, the FIG. 4B sonogram is an image slice that runs along the width of a patient.

FIG. 4A relates not only to the first algorithm, but also to an interactive display as part of the visual feedback 144.

The matrix array 160 has a current field of view 314 that partially includes ribs 404, 408 and partially (and here almost entirely) includes a heart 412. The first algorithm calculates blockage boundary lines 416, 420 that correspond to the boundary between good ultrasound beams and ones that are bad due to blockage by the ribs 404, 408.

Coherence of channel data is used to detect blockage. Each channel delivers its respective radiofrequency (RF) data magnitude associated with its respective fixed transducer element 170 or patch of elements. As ultrasound echoes return, their incident pressures on the elements 170 are sampled quickly and periodically. The samples are delayed with respect to each other according to the line-of-sight travel time geometry of the field point being evaluated. Here, "coherence" means similarity among data recorded by different channels of an array after applying the above-mentioned receiving focusing delays.

One gauge of coherence is a beam summed-data-based coherence estimation method, such as the one described in U.S. Patent Publication No. 2009/0141957 to Yen et al., the entire disclosure of which is incorporated herein by reference.

Figure 5:
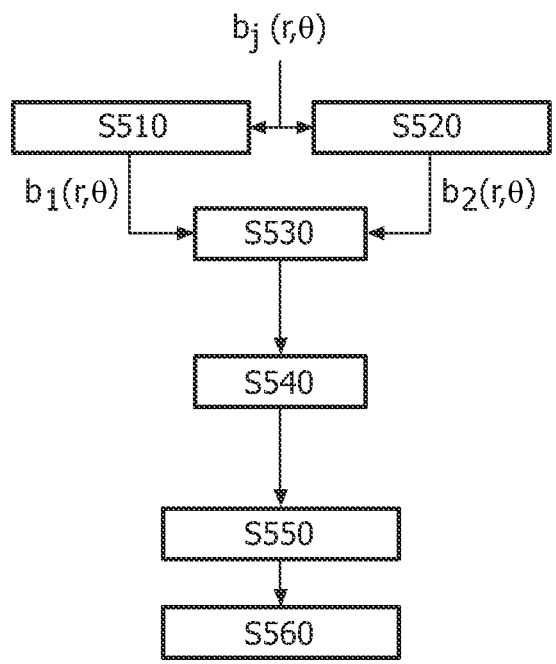
FIG. 5 is a flow chart, and formula list, relating to FIG. 4A.

The estimation method can be tailored to detecting rib and lung blockage, and is demonstrated below using two beamformers. Let $s_j(r, \theta)$ denote the (real-valued) channel data at depth r received by the j-th channel after applying the focusing delay, and let $C_1$ and $C_2$ denote the set of channels used in the first and the second beamformer, respectively. The output of the k-th (k=1, 2) beamformer is $b_k(r, \theta)$, the formula for which is shown in FIG. 5. When all the channel data $s_j(r, \theta)$ are identical across channels, $b_1(r, \theta)$ and $b_2(r,$ θ) will be highly correlated no matter how $C_1$ and $C_2$ are chosen. On the other hand, when the channel data are mainly contributed by scatterers in sidelobe regions, the correlation between $b_1$ and $b_2$ can drop significantly if $C_1$ and $C_2$ are properly chosen. $C_1$ and $C_2$ can be complementary, interleaving apertures. In short, it is possible to distinguish between on-axis signals and off-axis signals based on correlation between $b_1$ and $b_2$. The output of the correlator is the correlation coefficient $\rho(r, \theta)$ of $b_1$ (r, θ) and $b_2$(r, θ) defined as listed in FIG. 5, where w is a real symmetric weighting function. $\rho(r, \theta)$ is then lowpass filtered to get a smoothed correlation map $\hat{\rho}(r, \theta)$ which is used for blockage detection. A flow diagram for the algorithm, i.e., the "first algorithm", is shown in FIG. 5. Sums of $s_j$ (r, θ) are taken for $C_1$ (step S510) and for $C_2$ (step S520). They are correlated to calculate the correlation coefficient ρ(r, θ) (step S530) which is low-pass filtered (step S540) to produce the smoothed correlation map ρ(r, θ) used for blockage detection (step S550). The edge lines are then generated for the inverted "V" display (step S560).

In a specific example, the data is acquired at 32 MHz sampling rate in a pulse inversion (PI) mode using a probe having 80 elements 170. Each frame has 44 beams and the beam density is 0.4944 beam/degree. The center frequency is 1.3 and 2.6 MHz on transmit and on receive, respectively. $C_1=\{20\text{-}22, 26\text{-}28, 32\text{-}34, 38\text{-}40, 44\text{-}46, 50\text{-}52, 56\text{-}58\}$ and $C_2=\{23\text{-}25, 29\text{-}31, 35\text{-}37, 41\text{-}43, 47\text{-}49, 53\text{-}55, 59\text{-}61\}$. The weighting function w used in the correlator is a 51 (axially or in the r direction) by 1 (laterally or in the θ direction) boxcar and the smoothing filter is a 501 by 3 boxcar. Due to the periodic structure of the apertures, sensitivity of the correlation coefficient ρ to off-axis signals varies periodically with the direction of off-axis signals. This periodicity can be alleviated by randomizing sub-aperture sizes while still keeping both apertures complementary.

To verify whether a beam is blocked, a count is made of the number of points with a correlation coefficient ($\hat{\rho}$) higher than 0.55 between 72 and 180 mm in depth. If at least 400 points (at 32 MHz sampling rate) in a beam have high coherence, this beam is considered penetrating into tissue. Otherwise it is considered blocked by a rib.

Referring back to FIG. 4A, and counting the 80 beams from left to right, perhaps the $20^{th}$ beam exhibits high coherence; whereas, the $19^{th}$ beam does not exhibit high coherence. Thus, the first blockage boundary line 416 is shown in FIG. 4A at the $19^{th}$ beam. Likewise, if the $59^{th}$ beam exhibits high coherence, but the $60^{th}$ beam does not exhibit high coherence, the second blockage boundary line 420 is placed in coincidence with the $60^{th}$ beam.

The upper bound of the depth range is not critical. 72 mm, much larger than the depth of human ribs in general, can be chosen as the lower bound because high coherence factor values might be present in regions right below a rib due to multiple reflections (or reverberation) and such reflections tend to fade away with depth.

The apertures described do not include channels in both ends of the full aperture. Though apertures can be extended to include those channels, the number of blocked beams might be underestimated if large apertures are used. This is because the correlation coefficient of complementary aperture outputs could still be high if part of the large complementary apertures is not blocked.

Though the embodiment above uses 2D images acquired with a 1D probe, the methodology can be applied to matrix probes and therefore 3D volumetric imaging to guide novice users to perform volumetric acquisitions.

FIG. 4A also depicts an image that can be displayed for interactively guiding the clinician. The image of the heart 412 can be implemented as the segment(s) defining the heart by virtue of the coarse segmentation (step S244). The heart 412 is barely but partially outside the field of view 314. As the clinician shifts the probe 302 according to visual feedback 144 on-screen or in the form a green light 180 on the probe, the FIG. 4A image updates in real time. The inverted "V" composed of boundary lines 416 and 420 can easily be made to fully encompass the desired organ, here a heart. A FIG. 4A image, as part of the visual feedback 144, may supplement steps S212, S214 and S255 described above in connection with FIGS. 2A and 2B.

To optimize probe positioning, the span of V's can be enlarged through the use of an x-plane display.

Analogous to FIG. 4A, FIG. 4B relates not only to the second algorithm, but also to an interactive display as part of the visual feedback 144.

The matrix array 160 has a current field of view 314 that includes a heart 424 and part of a lung 428. The second algorithm calculates a blockage boundary line 432 that corresponds to the boundary between good ultrasound beams and ones that are bad due to blockage by the lung 428.

In the second algorithm, the center frequency of RF data acquired in PI modes is used as the parameter to distinguish lung tissue from heart tissue.

Figure 6A:
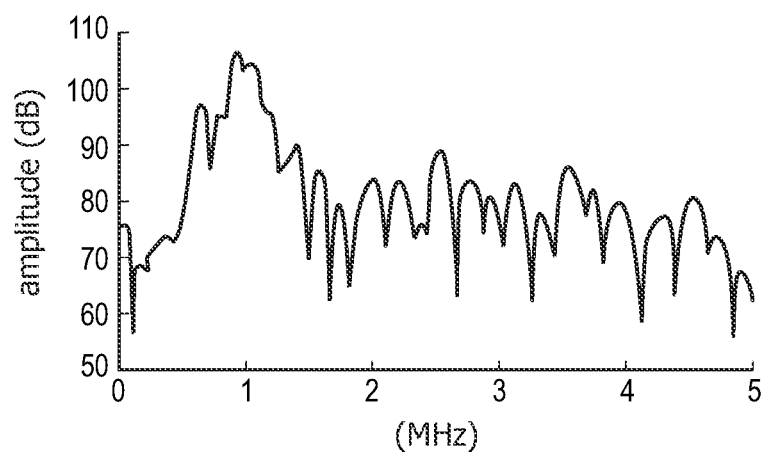
FIGS. 6A, 6B and 6C are, respectively, exemplary graphs of radiofrequency data used to distinguish lung tissue from heart tissue, and an algorithm used in the distinguishing, in accordance with the present invention.
Figure 6B:
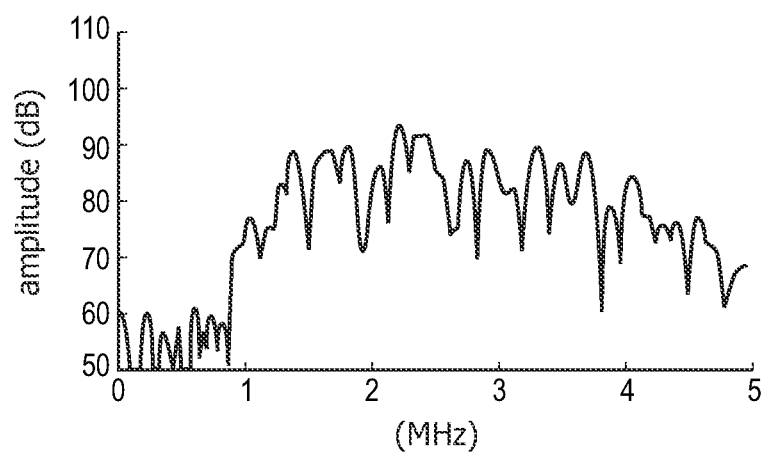

Sample RF data with a transmit center frequency of 2.1 MHz is shown in FIGS. 6A and 6B. The FIG. 6A graph represents the interrogation of lung tissue; whereas, the FIG. 6B graph represents the interrogation of heart tissue. Lung and heart tissue look more different in pulse inversion imaging than in conventional imaging. For example, lung tissue responded better to lower frequencies.

The FIG. 6A graph resulted from linear response of the lung tissue to self-demodulated signals. With wideband transmission, after nonlinear propagation the summation of the positive and the negative pulse will present a finite signal around 1 MHz, roughly half of the center frequency on transmit, a phenomenon called self-demodulation. Lung tissue responds to this low-frequency signal better than heart tissue. On the other hand, compared to lung tissue, heart tissue tends to favor higher frequency components in a PI mode because its stronger motion results in less perfect cancellation at higher frequencies.

Part of the second algorithm involves estimating the center frequency of the RF data. Let r(n) be a sampled A-line signal and R (n) be its complex envelope. $f_c$(n), the local center frequency of r(n), is related to R (n) by $$\arg\{R(n+1)R^*(n)\} \cong \frac{\arg\{R(n+1)R^*(n-1)\}}{2} \cong \frac{2\pi f_c(n)}{f_s}, \quad (1)$$

where arg{•} denotes phase/argument and A is the sampling rate. Estimators of $f_c$ (n) can be derived based on (1). An example of an estimator is:

$$\hat{f}_c(n) \equiv \frac{\arg\left\{\sum_{i=-m}^{i=m} w(i)R(n+i+1)R^*(n+i-1)\right\}}{4\pi} f_s \quad (2)$$

as the estimator. Averaging based on the window function w(i) reduces variance.

In one example, transmitting is at 2.1 MHz in a high resolution mode, the sampling rate is 32 MHz and the beam density is 0.72 beam/degree. One image or frame consists of 64 beams with 2 transmits per beam. The RF echoes in a frame are denoted as $\{r_p(n, \theta), r_n(n, \theta)\}$, where the subscripts p and n stand for positive and negative pulse on transmit respectively, and n and $\theta=\theta(k)$ (k is the beam index) denote time index and angle respectively.

Figure 6C:
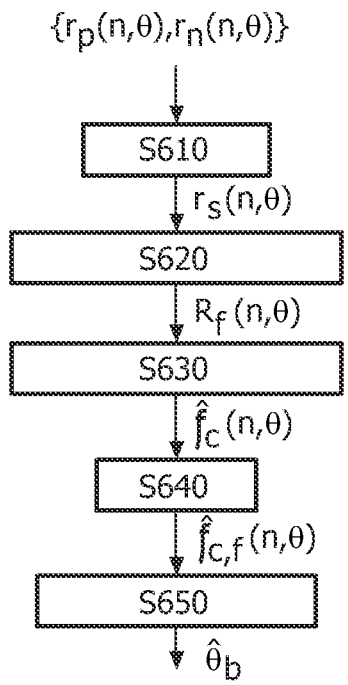

FIG. 6C shows the flow diagram of first version of the second algorithm, where $r_s(n, \theta) \equiv r_p(n, \theta) + r_n(n, \theta)$, $R_f(n, \theta) \equiv r_s(n, \theta) \otimes h(n)$, $\otimes$ denotes convolution, and h(n) is a 121-tap single-sided complex bandpass filter between 0.95 and 2.05 MHz. The center frequency map $\hat{f}_c(n, \theta)$ is obtained beam by beam based on equation (2) with a 301-tap Hamming window, and then smoothed by a 301 (axially or in the n direction) by 5 (laterally or in the $\theta$ direction) boxcar filter to get $\hat{f}_{c,f}(n, \theta)$. The last step is to estimate the boundary angle between heart and lung using the smoothed center frequency map $\hat{f}_{c,f}(n, \theta)$. The steps in FIG. 6C are summation (step S610), complex temporal filtering (step S620), center frequency estimation (step S630), 2D filtering (step S640) and boundary estimation (step S650).

Estimation of the boundary angle involves multiple thresholding. Starting with the first thresholding relation: For a beam (i.e., give a $\theta$) to qualify as a heart region, the center frequency has to satisfy the following condition:

$$\frac{1}{1501} \sum_{m=0}^{1500} \hat{f}_{c,f}(n+m, \theta) \geq f_{u1} \text{ for all } n \in [1500, 2500]. \quad (3)$$

That is, only if the average center frequencies between the 1500th and 3000th points (between 36 mm and 72 mm), between the 1501st and 3001st points, ..., and between the 2500th and 4000th points (between 60 mm and 96 mm) are all no lower than $f_{u1}$, can a beam be considered to be passing through heart tissue. The collection of the index of qualified beams is denoted as the set $A_1$. For example, $A_1=\{3, 4, \ldots, 32\}$ (noting that the 64 beams are counted from right to left in FIG. 4B and that the first two and last two beams do not qualify because of the spatial smoothing filter) for $f_{u1}=1.37$ MHz. Accordingly, the boundary angle can be estimated as the average angle over beams 32 and 33, $\theta(k)$ being an increasing function of k. The blockage boundary line 432 corresponds to the boundary angle.

The lung tissue can never appear on the right side of the heart (from the perspective patient) as long as the probe 302 is correctly positioned, unless the image shown in FIG. 4B is, in effect, flipped. We can therefore always estimate the boundary based on the leftmost beam satisfying the condition defined in (3). For example, if $A_1=\{14, 15, \ldots, 32\}$, the boundary angle still could be estimated as the average angle over beams 32 and 33.

Robustness of lung identification can be improved by including additional criteria. The second threshold is used to detect regions with very low center frequency: Given a beam angle $\theta$, if the center frequency satisfies $$\frac{1}{501} \sum_{m=0}^{500} \hat{f}_{c,f}(n+m, \theta) < f_1 \text{ for any } n \in [1750, 3750], \quad (4)$$

this beam can be considered passing through lung tissue. The collection of the index of beams satisfying (4) is denoted as $A_2$. $A_2=\{3, 4, \ldots, 32\}$ in the case shown in Error! Reference source not found. for $f_1=1.27$ MHz and therefore has no conflict with the corresponding $A_1$.

The third (and the last) threshold is used to detect regions with very high center frequency: Given a beam angle $\theta(k)$. if the center frequency satisfies $$\frac{1}{2001} \sum_{n=2000}^{4000} \hat{f}_{c,f}[n, \theta(k+m)] > f_{u2} \text{ for all } m \in \{-2, -1, 0, 1, 2\}, \quad (5)$$

this beam is considered to be passing through heart tissue. That is, if 5 consecutive beams present very high center frequency, the central beam has a high chance of passing heart tissue. The collection of the index of beams satisfying (5) is denoted as $A_3$.

In practice, $A_1$, $A_2$ and $A_3$ might not be consistent with each other. For example, the intersection of $A_1$ and $A_2$ might be nonempty meaning that some beam could be considered passing both heart and lung tissue. Accordingly, the collections may be prioritized. Specifically $A_3$ (the very high frequency condition defined in (5)) is given the highest priority and $A_1$ (the high frequency condition defined in (3)) is given the lowest priority. The "adjusted heart tissue set" is defined as $$A_h = \{k | k \in A_1 \text{ and } k < l \text{ for any } l \in A_2 \text{ that is larger than } \max(A_3)\}, \quad (6)$$

where $\max(A_3)$ is the maximum element of $A_3$ and is defined as $-\infty$ if $A_3$ is empty. The following is an equivalent definition:

$$A_h = \{k | k \in A_1 \text{ and } k < l \text{ for any } l \in A'_2\} \quad (7)$$

where $$A'_2 = \{l | l \in A_2 \text{ and } l > j \text{ for any } j \in A_3\}. \quad (8)$$

The boundary between heart and lung is estimated based on the largest element of $A_h$. For example, if $A_1=\{5, 6, \ldots, 50\}$, $A_2=\{3,4,49,50,51\}$ and $A_3=\{11,12,13\}$, then $A'_2=\{49,50, 51\}$, $A_h=\{5, 6, \ldots, 48\}$, and the estimated boundary angle $\hat{\theta}_b$ is the average angle over beams 48 and 49. An empty $A_h$ indicates lung tissue occupying the whole image. If $A_h$ is not empty, $$\hat{\theta}_b = 1/2\{\theta[\max(A_h)] + \theta[\max(A_h)+1]\} = \theta[\max(A_h)] + 1/2\Delta\theta, \quad (9)$$

where $\Delta\theta = \theta(k+1) - \theta(k)$. Because the 2D smoothing filter deteriorates beams on the sides, it is concluded that no lung tissue appears in the image if $$\max(A_h) \geq \text{(beam number)} -$$

$$\text{(half the lateral dimension of the 2D smoothing filter)} = 64 - \frac{5-1}{2} = 62.$$

The role of $f_{u1}$ is much more important than that of $f_1$, but occasionally existence of $A_2$ contributes positively in determining the boundary. To recap, in this first version of the second algorithm, $f_{u1}=1.37$ MHz, $f_1=1.27$ MHz, and $f_{u2}=\infty$.

A second version of the second algorithm also pertains to 1D probes and for

Figure 7:
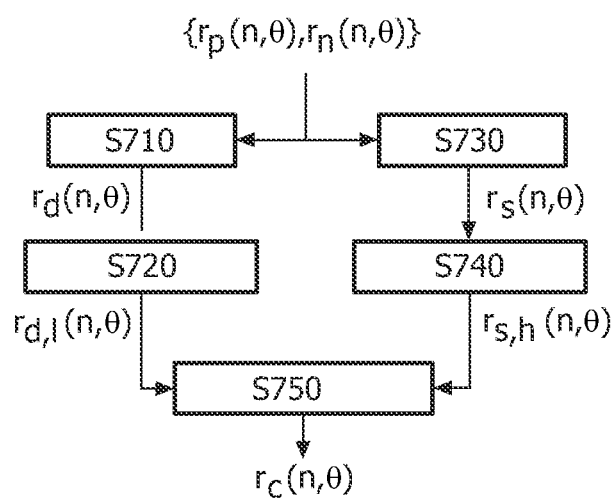
FIG. 7 is a flow chart representative of an exemplary lung identification algorithm based on a one-dimensional probe.

PI data. As mentioned above, lung tissue responds to low-frequency signal components well in a linear fashion and motion causes less perfect cancellation at higher frequencies in heart tissue in a PI mode. This implies the possibility of performance improvement by replacing $r_s(n, \theta)$ with a composite signal $r_c(n, \theta)$ in the signal processing chain shown in FIG. 6C. For this reason, there is a second version of the second algorithm. FIG. 7 shows how $r_c(n, \theta)$ is formed, where $r_d(n, \theta) \equiv r_p(n, \theta) - r_n(n, \theta)$ which is step S710, $r_{d,l}(n, \theta) \equiv r_d(n, \theta) \otimes h_l(n)$ which is step S720, step S730 is identical to step S610, $r_{s,h}(n, \theta) \equiv r_s(n, \theta) \otimes h_h(n)$ which is step S740, $r_c(n, \theta) \equiv w_d r_{d,l}(n, \theta) + w_s r_{s,h}(n, \theta)$ which is step S750, $h_l(n)$ is a 101-tap real lowpass filter cutting off at 0.8 MHz, and $h_u(n)$ is a 101-tap real highpass filter cutting off at 1.15 MHz. Echoes from lung tissue favor $r_{d,l}(n, \theta)$ (because it responds to low-frequency components well) and echoes from heart tissue favor $r_{s,h}(n, \theta)$ (because of more motion). $w_d$ and $w_s$ are weights used to balance the two forces. The signal processing following $r_c(n, \theta)$ remains the same as that following $r_s(n, \theta)$ in FIG. 6C. Exemplary parameters are $w_d=1.2$, $w_s=1$ $f_{u1}=1.4$ MHz, $f_l=1.2$ MHz, and $f_{u2}=1.5$ MHz.

A matrix probe version of the second algorithm is based on the second version—composite signals are used for center frequency estimation. RF data can be collected, for example, using penetration imaging mode with PI enabled and a center frequency of 2.2 MHz. Lateral and elevational widths can be maximal.

Each volume has RF echoes $\{r_p(n, \theta, \phi), r_n(n, \theta, \phi)\}$ with 40 $\theta$ (lateral) values and 33 $\phi$ (elevational) values. The lateral beam density is 0.41 beam per degree.

Figure 8:
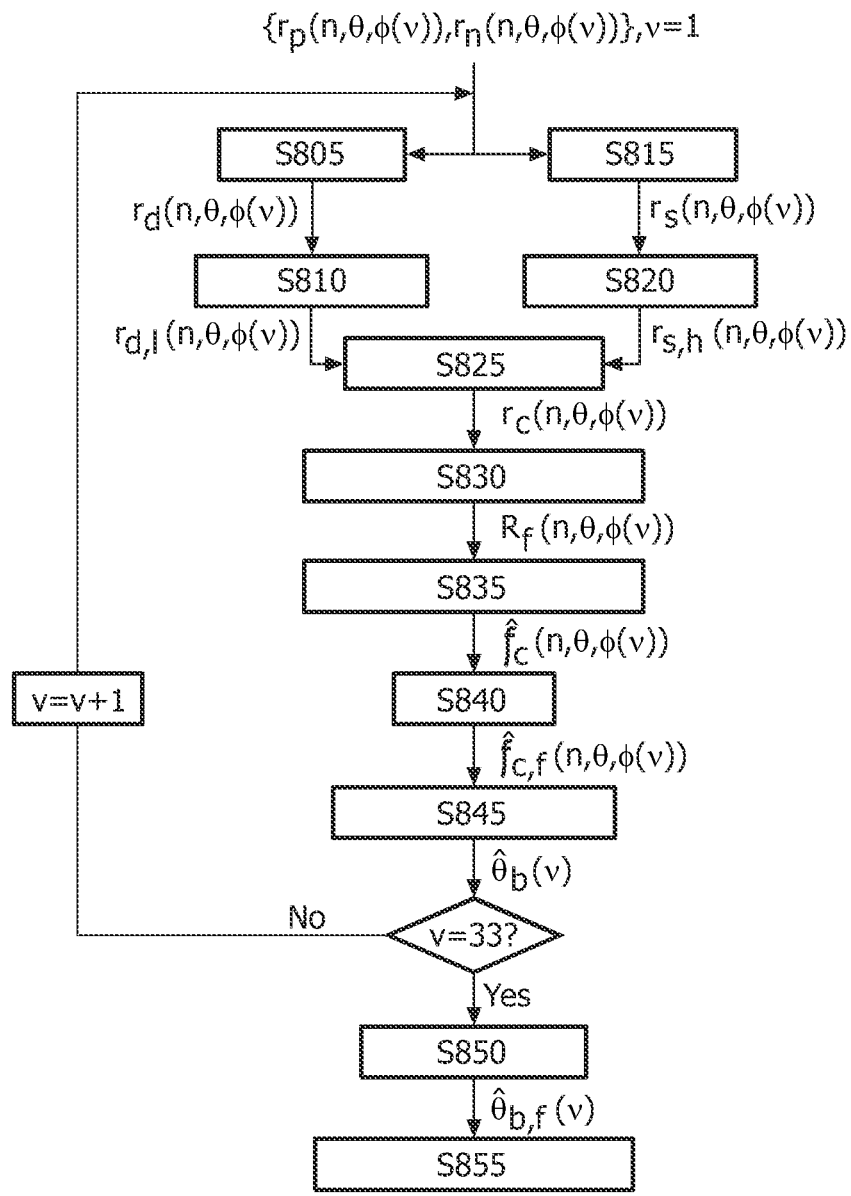
FIG. 8 is a flow chart representative of an exemplary lung identification algorithm based on a matrix probe.

FIG. 8 shows the flow diagram of the matrix probe version of the second algorithm, with the temporal sampling rate at 16 MHz. The steps are: subtraction (step S805), low-pass filtering (step S810), summation (step S815), high-pass filtering (step S820), weighted summation (step S825), complex temporal filtering (step S830), center frequency estimation (step S835), 2D filtering (step S840), boundary estimation (step S845), median filtering (step S850) and visualization across planes (step S855). In short, $\phi = \varphi(v)$, $r_d(n, \theta, \phi) \equiv r_p(n, \theta, \phi) - r_{ii}(n, \theta, \phi)$, $r_s(n, \theta, \phi) \equiv r_p(n, \theta, \phi) + r_n(n, \theta, \phi)$, $r_{d,l}(n, \theta, \phi) \equiv r_d(n, \theta, \phi) \otimes h_l(n)$, $r_{s,h}(n, \theta, \phi) \equiv r_s(n, \theta, \phi) \otimes h_h(n)$, $r_c(n, \theta, \phi) \equiv w_d r_{d,l}(n, \theta, \phi) + w_s r_{s,h}(n, \theta, \phi)$, $h_l(n)$ is a 51-tap real lowpass filter cutting off at 0.8 MHz, $h_u(n)$ is a 51-tap real highpass filter cutting off at 1.3 MHz, $w_d=2$, and $w_s=1$. The complex envelope $R_f(n, \theta, \phi) \equiv r_c(n, \theta, \phi) \otimes h(n)$, where h(n) is a 61-tap single-sided complex bandpass filter between 0.95 and 2.05 MHz. In each elevational plane, the center frequency map $\hat{f}_c(n, \theta, \phi)$ is obtained beam by beam based on equation (2) with a 151-tap Hamming window, and then smoothed by a 151 (in the n direction) by 3 (in the $\theta$ direction) boxcar filter to get $\hat{f}_{c,f}(n, \theta, \phi)$.

For boundary estimation, the following are defined:

$$A_{1,v} \equiv \tag{10}$$

$$\left\{ k \,\middle|\, \frac{1}{751} \sum_{m=0}^{750} \hat{f}_{c,f}(n+m, \theta(k), \phi(v)) \geq f_{u1} \text{ for all } n \in [750, 1250] \right\}.$$

$$A_{2,v} \equiv \tag{11}$$

$$\left\{ k \,\middle|\, \frac{1}{251} \sum_{m=0}^{250} \hat{f}_{c,f}(n+m, \theta(k), \phi(v)) < f_l \text{ for any } n \in [875, 1875] \right\},$$

and $$A_{3,v} \equiv \tag{12}$$

$$\left\{ k \,\middle|\, \frac{1}{1001} \sum_{n=1000}^{2000} \hat{f}_{c,f}(n, \theta(k+m), \phi(v)) > f_{u2} \text{ for all } m \in \{-1, 0, 1\} \right\},$$

where $f_{u1}=1.38$ MHz. Equivalently $f_l \equiv 0$, $f_{u2} \equiv \infty$, $A_{2,v}$ and $A_{3,v}$ are empty, and the adjusted heart tissue set $A_{h,v}=A_{1,v}$.

The boundary angle between heart and lung in the v-th plane is $$\hat{\theta}_b(v) \equiv \begin{cases} \theta(1) - \frac{1}{2}\Delta\theta & \text{if } A_{h,v} \text{ is empty} \\ \theta(40) + \frac{1}{2}\Delta\theta & \text{if } \max(A_{h,v}) \geq 40 - \frac{3-1}{2} = 39. \\ \theta[\max(A_{h,v})] + \frac{1}{2}\Delta\theta & \text{otherwise} \end{cases} \tag{13}$$

A 5-tap median filter (a function of v) in the elevational direction is then applied to $\hat{\theta}_b(v)$ and the output is denoted as $\hat{\theta}_{b,f}(v)$. From the filtered boundary angles $\hat{\theta}_{b,f}(v)$, a map indicating heart region can be derived to provide cross-plane visualization. To remove outliers around the boundary between heart and lung which appear occasionally, only the largest connected region is displayed. The clinician can use the FIG. 4B display to interactively manipulate the probe 302 so as to avoid the lung, in step S226.

An imaging steering apparatus includes sensors and an imaging processor configured for: acquiring, via multiple ones of the sensors and from a current position, and current orientation, an image of an object of interest; based on a model, segmenting the acquired image; and determining, based on a result of the segmenting, a target position, and target orientation, with the target position and/or target orientation differing correspondingly from the current position and/or current orientation. An electronic steering parameter effective toward improving the current field of view may be computed, and a user may be provided instructional feedback in navigating an imaging probe toward the improving. A robot can be configured for, automatically and without need for user intervention, imparting force to the probe to move it responsive to the determination.

In addition to making diagnostic cardiac examination performable by nurses or other clinicians who may be untrained specifically in sonography, the apparatus 100 can guide novice sonographers. The apparatus 100 can feature, for this purpose or this mode, a regular (grayscale) sonogram, along with the visual feedback 144 described herein above. Alternatively, the novel visual feedback 144 of the apparatus 100 can speed up the work flow of trained or experienced sonographers.

While the invention has been illustrated and described in detail in the drawings and foregoing description, such illustration and description are to be considered illustrative or exemplary and not restrictive; the invention is not limited to the disclosed embodiments. For example, user feedback onscreen in the form of probe steering instructions can be supplemented, or replaced, by audible, spoken instructions.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. A medical-imaging view steering apparatus comprising:
    an imaging probe having an orientation, and an image space;
    a user-guidance processor configured for presenting user instructions to propose user action toward improving a field of view of an object of interest, the user instructions including an instruction to pause movement of the imaging probe and a directional indicator indicating a direction in which to shift the imaging probe orientation; and
    an imaging processor configured for:
        acquiring, utilizing said imaging probe, an ultrasound image of the object of interest, when said object of interest is at least partially located in said image space;
        using an anatomical model, segmenting the acquired ultrasound image to identify the object of interest when the object of interest is at least partially located in said image space; and
        determining for said imaging probe, based on said segmenting of the acquired ultrasound image, and a desired target orientation of the object of interest in the image space, appropriate user instructions to be presented so as to achieve the desired target orientation,
    wherein said appropriate user instructions are determined taking into account rib curvature in a longitudinal direction.

2. A medical-imaging view steering apparatus comprising:
    an imaging probe having an orientation, and an image space;
    a user-guidance processor configured for presenting user instructions to propose user action toward improving a field of view of an object of interest, the user instructions including an instruction to pause movement of the imaging probe and a directional indicator indicating a direction in which to shift the imaging probe orientation; and
    an imaging processor configured for:
        acquiring, utilizing said imaging probe, an ultrasound image of the object of interest, when said object of interest is at least partially located in said image space;
        using an anatomical model, segmenting the acquired ultrasound image to identify the object of interest when the object of interest is at least partially located in said image space; and
        determining for said imaging probe, based on said segmenting of the acquired ultrasound image, and a desired target orientation of the object of interest in the image space, appropriate user instructions to be presented so as to achieve the desired target orientation,
    wherein the user instructions further comprise visual instructions, and
    wherein the user-guidance processor is further configured to present user instructions by means of lights located on the imaging probe.

3. The apparatus of claim 2, wherein the user-guidance processor is further configured to indicate a proposed imaging probe movement direction by the color of the lights.

4. A medical-imaging view steering apparatus comprising:
    an imaging probe having an orientation, and an image space;
    a user-guidance processor configured for presenting user instructions to propose user action toward improving a field of view of an object of interest, the user instructions including an instruction to pause movement of the imaging probe and a directional indicator indicating a direction in which to shift the imaging probe orientation; and
    an imaging processor configured for:
        acquiring, utilizing said imaging probe, an ultrasound image of the object of interest, when said object of interest is at least partially located in said image space;
        using an anatomical model, segmenting the acquired ultrasound image to identify the object of interest when the object of interest is at least partially located in said image space; and
        determining for said imaging probe, based on said segmenting of the acquired ultrasound image, and a desired target orientation of the object of interest in the image space, appropriate user instructions to be presented so as to achieve the desired target orientation,
    wherein the user instruction to pause movement of the imaging probe further comprises a pause/go indicator light.

5. The apparatus of claim 4, wherein the pause/go indicator light is one color when instructing to move the imaging probe, and another color when instructing to pause movement of the imaging probe.

6. The apparatus of claim 5, wherein the pause/go indicator light is located on the imaging probe.

7. The apparatus of claim 5, wherein the pause/go indicator light further comprises a user instruction to look for further user instructions on proposed probe movement.

8. The apparatus of claim 4, wherein the user guidance processor is further configured for presenting a progress indicator indicating progress toward achieving the desired target orientation.

9. The apparatus of claim 4, wherein the user-guidance processor and the imaging processor are further configured to be operable during a clinical ultrasound procedure in a first stage during which the imaging probe is moved until at least a portion of the object of interest is detected in the image space, and in a second stage during which movement of the imaging probe is frequently paused for the presentation of further user instructions.

10. The apparatus of claim 4, wherein said target orientation is in an axial direction of said probe, and
    wherein said model-provided segmentation is with respect to said axial direction.

11. The apparatus of claim 4, further configured for deciding, based on image segmentation, that it has detected, in the acquired ultrasound image, at least part of said object of interest.

12. The apparatus of claim 4, said apparatus being further configured for presenting said user instructions to propose user action toward achieving the desired target orientation.

13. The apparatus of claim 4, said user instructions relating to either translating, or tilting, said imaging probe in order to achieve said desired target orientation.

14. The apparatus of claim 4, said apparatus being further configured for computing an electronic steering parameter for steering the imaging probe image space, said apparatus being configured for electronically steering using the computed electronic steering parameter.

15. The apparatus of claim 4, wherein the user instructions further comprise visual instructions.

16. The apparatus of claim 4, wherein the user-guidance processor is further configured to present user instructions as textual instructions on a display screen.

17. The apparatus of claim 4, wherein the user-guidance processor is further configured to present user instructions as auditory instructions.

18. The apparatus of claim 17, wherein the auditory instructions further comprise artificial speech.

19. A medical-imaging view steering apparatus comprising:
   an imaging probe having an orientation, and an image space;
   a user-guidance processor configured for presenting user instructions to propose user action toward improving a field of view of an object of interest, the user instructions including an instruction to pause movement of the imaging probe and a directional indicator indicating a direction in which to shift the imaging probe orientation; and
   an imaging processor configured for:
      acquiring, utilizing said imaging probe, an ultrasound image of the object of interest, when said object of interest is at least partially located in said image space;
      using an anatomical model, segmenting the acquired ultrasound image to identify the object of interest when the object of interest is at least partially located in said image space; and
      determining for said imaging probe, based on said segmenting of the acquired ultrasound image, and a desired target orientation of the object of interest in the image space, appropriate user instructions to be presented so as to achieve the desired target orientation,
   wherein the user guidance processor is further configured to present the user instruction to pause movement of the imaging probe during the segmenting of an acquired image.

* * * * *